United States Patent
Hamada et al.

(10) Patent No.: US 7,897,683 B2
(45) Date of Patent: Mar. 1, 2011

(54) MEDICAL ADHESIVE AND MEDICAL ADHESIVE TAPE OR SHEET

(75) Inventors: Atsushi Hamada, Osaka (JP); Tomonari Naito, Osaka (JP); Namiko Murayama, Osaka (JP); Miki Funahashi, Osaka (JP); Jun Ishikura, Osaka (JP)

(73) Assignee: Nitto Denko Corporation, Osaka (JP)

( * ) Notice: Subject to any disclaimer, the term of this patent is extended or adjusted under 35 U.S.C. 154(b) by 469 days.

(21) Appl. No.: 11/802,190

(22) Filed: May 21, 2007

(65) Prior Publication Data

US 2007/0275239 A1 Nov. 29, 2007

(30) Foreign Application Priority Data

| May 24, 2006 | (JP) | ............................. 2006-144150 |
| Oct. 10, 2006 | (JP) | ............................. 2006-276941 |
| Nov. 1, 2006 | (JP) | ............................. 2006-298209 |

(51) Int. Cl.
| C08L 33/00 | (2006.01) |
| C08L 43/04 | (2006.01) |
| C08L 31/02 | (2006.01) |
| C08F 2/16 | (2006.01) |
| C08F 2/22 | (2006.01) |
| C08K 5/00 | (2006.01) |
| B32B 7/12 | (2006.01) |
| B32B 9/04 | (2006.01) |
| A61F 13/02 | (2006.01) |

(52) U.S. Cl. .......................... 524/832; 524/81; 524/800; 524/804; 524/806; 428/343; 428/411.1; 604/307

(58) Field of Classification Search .................. 524/81, 524/800, 804, 806, 832
See application file for complete search history.

(56) References Cited

U.S. PATENT DOCUMENTS

| 4,716,194 | A |  | 12/1987 | Walker et al. |
| 5,543,151 | A | * | 8/1996 | Shirai et al. .................. 424/448 |
| 2003/0023018 | A1 | * | 1/2003 | Nakano et al. ............... 526/319 |
| 2004/0254276 | A1 | * | 12/2004 | Okada et al. ................. 524/272 |

FOREIGN PATENT DOCUMENTS

| EP | 0 224 795 | 6/1987 |
| EP | 0 624 635 | 11/1994 |
| EP | 1 486 548 | 12/2004 |
| JP | 6-23029 | 2/1994 |
| JP | 6-319793 | 11/1994 |

OTHER PUBLICATIONS

European Search Report issued Nov. 13, 2007 in the European application corresponding to the present U.S. application.

* cited by examiner

*Primary Examiner*—Vasu Jagannathan
*Assistant Examiner*—Karuna P Reddy
(74) *Attorney, Agent, or Firm*—Wenderoth, Lind & Ponack, L.L.P.

(57) ABSTRACT

The present invention provides a medical adhesive and a medical adhesive tape or sheet superior in the fixing performance, particularly perspiration-resistant fixing, which shows low skin irritation and suitable adhesive strength. The present invention provides a medical adhesive containing a water-dispersed copolymer obtained by copolymerizing 100 parts by weight of a monomer mixture containing (meth) acrylic acid alkyl ester and 0.005-2 parts by weight of a silane monomer copolymerizable with the ester, and an organic liquid component compatible with the copolymer; a medical adhesive containing a water-dispersed copolymer obtained by copolymerizing a monomer mixture containing (meth) acrylic acid alkyl ester and a silane monomer copolymerizable with the ester, and an organic liquid component compatible with the copolymer, wherein the gel fraction after crosslinking of the copolymer is 40-80 wt %, and the weight average molecular weight of a sol component after crosslinking is not less than 300000; and a medical adhesive tape or sheet having the medical adhesive at least on one surface of a support.

10 Claims, No Drawings

MEDICAL ADHESIVE AND MEDICAL ADHESIVE TAPE OR SHEET

TECHNICAL FIELD OF THE INVENTION

The present invention relates to a medical adhesive used for the field of medical hygiene material and the like. The present invention also relates to a medical adhesive tape or sheet used for adhesive bandage, surgical tape, first-aid adhesive tape, large-sized adhesive tape, dressing material, cataplasm and the like.

BACKGROUND OF THE INVENTION

For the purpose of protection of skin lesion, transdermal absorption of drugs and fixation of gauze or tube and the like to the skin, medical adhesive tapes and sheets using various medical adhesives have been conventionally developed. Since medical adhesive tapes and sheets are mostly adhered to the skin, adhesiveness to the skin, and further, an ability to fix a tube and the like having a repulsive force to the skin are required. Simultaneously, they are required to cause no pain or damage such as separation of stratum corneum to the skin, and the like.

As an adhesive used for an adhesive layer of a medical adhesive tape or sheet, an adhesive constituted of a (meth) acrylic acid ester polymer superior in the adhesiveness and moisture permeability, and less chemically irritative to the skin is generally used.

However, since the adhesive strength of adhesive constituted of a (meth)acrylic acid ester polymer is too high, an adhesive tape or sheet using the adhesive may cause pain or damage to the stratum corneum and epidermis of the skin upon peeling off from the skin.

Particularly, when an adhesive tape or sheet is repeatedly applied to the same part, a skin damage accompanying bleeding may be caused, posing a serious problem.

To reduce such physical irritation to the skin, gel adhesives obtained by adding, to a (meth)acrylic acid ester polymer, a large amount of an organic liquid component compatible with the polymer and subjecting the polymer to a crosslinking treatment have been proposed (e.g., see JP-A-6-23029 and JP-A-6-319793).

Such gel adhesives can reduce and disperse the stress applied to the skin surface upon peeling, while maintaining the high adhesiveness that (meth)acrylic acid ester polymers have. Accordingly, the adhesives can be used for transdermal patches and medical surgical tapes since they cause less physical irritation to the skin and extremely infrequent separation of stratum corneum and the like.

DISCLOSURE OF THE INVENTION

An adhesive tape or sheet obtained by laminating a gel adhesive as disclosed in each of the above-mentioned patent references on a support only insufficiently fixes a medical tube to the skin, and sometimes shows a remarkably degraded perspiration-resistant fixing performance particularly in the summer season when perspiration increases.

Most of the medical adhesives containing the adhesive disclosed in each of the above-mentioned patent references are produced in an organic solvent such as ethyl acetate and the like, and the current situation is not entirely preferable for the environmental hygiene.

The present inventors have conducted intensive studies in an attempt to solve the aforementioned problems and found that a medical adhesive that can sufficiently fix a medical instrument with a repulsive force such as a medical tube and the like to the skin and is superior in perspiration-resistant fixing can be obtained by dissolving an organic liquid component in a water-dispersed copolymer obtained by copolymerizing a silane monomer with a monomer mixture containing (meth)acrylic acid alkyl ester, at a particular rate.

The present inventors have further studied intensively and found that a medical adhesive comprising a water-dispersed copolymer obtained by copolymerizing a silane monomer copolymerizable with (meth)acrylic acid alkyl ester with a monomer mixture containing (meth)acrylic acid alkyl ester, and an organic liquid component compatible with the water-dispersed copolymer, and having particular physical properties sufficiently fixes a medical instrument with a repulsive force such as a medical tube and the like to the skin, and is superior in perspiration-resistant fixing performance, which resulted in the completion of the present invention.

That is, the present invention provides the following.

[1] A medical adhesive comprising a water-dispersed copolymer obtained by copolymerizing 100 parts by weight of a monomer mixture containing (meth)acrylic acid alkyl ester and 0.005-2 parts by weight of a silane monomer copolymerizable with the (meth)acrylic acid alkyl ester, and an organic liquid component compatible with the water-dispersed copolymer.

[2] The medical adhesive of the above-mentioned [1], wherein the monomer mixture containing the (meth)acrylic acid alkyl ester comprises 0.1-10 parts by weight of a carboxyl group-containing monomer copolymerizable with the (meth)acrylic acid alkyl ester in 100 parts by weight of the monomer mixture containing the (meth)acrylic acid alkyl ester.

[3] The medical adhesive of the above-mentioned [1] or [2], wherein the water-dispersed copolymer after crosslinking has a gel fraction of 30-80 wt %.

[4] A medical adhesive tape or sheet, comprising the medical adhesive of any one of the above-mentioned [1]-[3] on at least one surface of a support.

[5] A medical adhesive comprising a water-dispersed copolymer obtained by copolymerizing a monomer mixture containing (meth)acrylic acid alkyl ester and a silane monomer copolymerizable with the (meth)acrylic acid alkyl ester, and an organic liquid component compatible with the water-dispersed copolymer, wherein the gel fraction of the water-dispersed copolymer after crosslinking is 40-80 wt %, and the weight average molecular weight of a sol component of the water-dispersed copolymer after crosslinking is not less than 300000.

[6] The medical adhesive of the above-mentioned [5], wherein the gel fraction of the water-dispersed copolymer before crosslinking is not more than 30 wt %.

[7] The medical adhesive of the above-mentioned [5], wherein weight average molecular weight/number average molecular weight of the sol component of the water-dispersed copolymer after crosslinking is 3-7.

[8] The medical adhesive of any one of the above-mentioned [5]-[7], wherein the monomer mixture containing the (meth) acrylic acid alkyl ester comprises 0.1-10 parts by weight of a carboxyl group-containing monomer copolymerizable with the (meth)acrylic acid alkyl ester in 100 parts by weight of the monomer mixture containing the (meth)acrylic acid alkyl ester, and the water-dispersed copolymer is obtained by copolymerizing 0.005-2 parts by weight of the silane monomer copolymerizable with the (meth)acrylic acid alkyl ester and 100 parts by weight of the monomer mixture containing the (meth)acrylic acid alkyl ester.

[9] A medical adhesive tape or sheet, comprising the medical adhesive of any one of the above-mentioned [5]-[8] on at least one surface of a support.

EFFECT OF THE INVENTION

The medical adhesive of the present invention simultaneously shows appropriate adhesiveness, good fixing performance and perspiration-resistant fixing performance to the skin, and, even when applied to a medical adhesive tape or sheet and the like, suppresses physical irritation caused by detachment thereof from an adhered to a low level. In addition, since the medical adhesive of the present invention does not use an organic solvent for production thereof, it is preferable for the environmental hygiene.

BEST MODE FOR EMBODYING THE INVENTION

The present invention relates to a medical adhesive comprising a water-dispersed copolymer obtained by copolymerizing a monomer mixture containing (meth)acrylic acid alkyl ester and a silane monomer copolymerizable with the (meth)acrylic acid alkyl ester, and an organic liquid component compatible with the water-dispersed copolymer, and provides (1) a medical adhesive comprising a water-dispersed copolymer obtained by copolymerizing 100 parts by weight of a monomer mixture containing (meth)acrylic acid alkyl ester and 0.005-2 parts by weight of a silane monomer copolymerizable with the (meth)acrylic acid alkyl ester, and an organic liquid component compatible with the water-dispersed copolymer (hereinafter sometimes to be referred to as a first medical adhesive of the present invention), and (2) a medical adhesive comprising a water-dispersed copolymer obtained by copolymerizing a monomer mixture containing (meth)acrylic acid alkyl ester and a silane monomer copolymerizable with the (meth)acrylic acid alkyl ester, and an organic liquid component compatible with the water-dispersed copolymer, wherein the gel fraction of the water-dispersed copolymer after crosslinking is 40-80 wt %, and the weight average molecular weight of a sol component of the water-dispersed copolymer after crosslinking is not less than 300000 (hereinafter sometimes to be referred to as a second medical adhesive of the present invention).

In the present specification, the medical adhesive of the present invention includes both the above-mentioned first and second medical adhesives of the present invention.

The medical adhesive of the present invention is crosslinked by a silane monomer.

While the monomer mixture containing (meth)acrylic acid alkyl ester used for the medical adhesive of the present invention is a monomer mixture comprising (meth)acrylic acid alkyl ester (preferably 50-100 wt %) as a main component, the below-mentioned silane monomer is not included in the monomer mixture in this context.

As the (meth)acrylic acid alkyl ester, a (meth)acrylic acid alkyl ester wherein the alkyl moiety is straight chain or branched alkyl having not less than 1, preferably not more than 15, more preferably 1-9, carbon atoms is used. Specifically, for example, (meth)acrylic acid alkyl ester having straight chain or branched alkyl group such as methyl (meth)acrylate, ethyl(meth)acrylate, n-butyl(meth)acrylate, isobutyl(meth)acrylate, pentyl(meth)acrylate, hexyl (meth)acrylate, heptyl(meth)acrylate, n-octyl(meth)acrylate, isooctyl (meth)acrylate, 2-ethylhexyl(meth)acrylate, n-nonyl (meth)acrylate, isononyl(meth)acrylate, decyl(meth)acrylate, undecyl(meth)acrylate, tridecyl(meth)acrylate and the like can be used. These can be used alone or in combination of two or more kinds thereof. Particularly, n-octyl acrylate, isooctyl acrylate, 2-ethylhexyl acrylate, n-nonyl acrylate, isononyl acrylate, methyl methacrylate, ethyl methacrylate and n-butyl methacrylate are preferable.

The silane monomer copolymerizable with (meth)acrylic acid alkyl ester to be used for the medical adhesive of the present invention is not particularly limited as long as it is a polymerizable compound having a silicon atom and copolymerizable with (meth)acrylic acid alkyl ester. A silane compound having a (meth)acryloyl group such as (meth)acryloyloxyalkylsilane derivative and the like is preferable in view of the superior copolymerizability with (meth)acrylic acid alkyl ester. Examples of the silane monomer include 3-(meth)acryloyloxypropyltrimethoxysilane, 3-(meth)acryloyloxypropyltriethoxysilane, 3-(meth)acryloyloxypropylmethyldimethoxysilane, 3-(meth)acryloyloxypropylmethyldiethoxysilane and the like. These silane monomers can be used alone or in combination with two or more kinds thereof. Particularly, 3-methacryloyloxypropyltrimethoxysilane, 3-methacryloyloxypropyltriethoxysilane and 3-acryloyloxypropyltrimethoxysilane are preferable.

In addition to the above-mentioned, as a silane monomer, for example, vinyltrimethoxysilane, vinyltriethoxysilane, 4-vinylbutyltrimethoxysilane, 4-vinylbutyltriethoxysilane, 8-vinyloctyltrimethoxysilane, 8-vinyloctyltriethoxysilane, 10-methacryloyloxydecyltrimethoxysilane, 10-acryloyloxydecyltrimethoxysilane, 10-methacryloyloxydecyltriethoxysilane, 10-acryloyloxydecyltriethoxysilane and the like can be used.

The silane monomer constituting the first medical adhesive of the present invention in an amount of 0.005-2 parts by weight, preferably 0.005-1 part by weight, more preferably 0.01-0.4 part by weight, is copolymerized per 100 parts by weight of a monomer mixture containing (meth)acrylic acid alkyl ester. When the copolymerization amount of the silane monomer exceeds 2 parts by weight, sufficient fixing performance may not be afforded, and when it is less than 0.005 part by weight, the cohesive force may easily decrease due to the insufficient polymer strength and the problem of adhesive residue and the like may be caused.

In the second medical adhesive of the present invention, the above-mentioned silane monomer in an amount of preferably 0.005-2 parts by weight, more preferably 0.005-1 part by weight, further more preferably 0.01-0.4 part by weight, is copolymerized relative to 100 parts by weight of the monomer mixture containing (meth)acrylic acid alkyl ester.

When the copolymerization amount of the silane monomer exceeds 2 parts by weight, sufficient fixing performance may not be afforded, and when it is less than 0.005 part by weight, the cohesive force may easily decrease due to the insufficient polymer strength and the problem of adhesive residue and the like may be caused.

In the medical adhesive of the present invention, by copolymerization of a silane monomer with a monomer mixture containing (meth)acrylic acid alkyl ester, the silane compound to be the crosslinking site becomes uniformly present in the molecule of the obtained copolymer. Consequently, while the medical adhesive of the present invention is of a water-dispersed type, the inner part and the outer side of the particles of the water-dispersed adhesive are uniformly crosslinked. As a result, superior cohesive force is afforded, and therefore, low skin irritation by the addition of an organic liquid component, and superior fixing performance and perspiration-resistant fixing performance are simultaneously achieved.

In the medical adhesive of the present invention, it is preferable that the above-mentioned monomer mixture containing (meth)acrylic acid alkyl ester should contain a carboxyl group-containing monomer copolymerizable with (meth) acrylic acid alkyl ester from the aspects of hydrolysis of the silane monomer and adjustment of the achieved adhesiveness.

The above-mentioned carboxyl group-containing monomer is contained in a proportion of preferably 0.1-10 parts by weight, more preferably 0.5-8 parts by weight, further more preferably 1-6 parts by weight, in 100 parts by weight of the monomer mixture containing (meth)acrylic acid alkyl ester, from the aspects of hydrolysis of the silane monomer and adjustment of the achieved adhesiveness.

When the amount of the carboxyl group-containing monomer is less than 0.1 part by weight, the silane monomer is not hydrolyzed and the crosslinking reaction is not promoted. As a result, the insolubilized content becomes smaller and the adhesive tends to remain upon peeling off. When the amount exceeds 10 parts by weight, problems occur in that the solution viscosity during polymerization reaction becomes high and the production of the adhesive becomes difficult.

The carboxyl group-containing monomer copolymerizable with (meth)acrylic acid alkyl ester is not particularly limited as long as it is a polymerizable compound having a carboxyl group in its structure and copolymerizable with (meth)acrylic acid alkyl ester. For example, (meth)acrylic acid, itaconic acid, maleic acid, maleic anhydride, 2-methacryloyloxyethylsuccinic acid and the like can be used. Particularly, acrylic acid and 2-methacryloyloxyethylsuccinic acid are preferable.

The water-dispersed copolymer constituting the medical adhesive of the present invention may be obtained, where necessary, by copolymerization of a monomer copolymerizable with (meth)acrylic acid alkyl ester other than the silane monomer and the carboxyl group-containing monomer. The monomer copolymerizable with (meth)acrylic acid alkyl ester other than the silane monomer and the carboxyl group-containing monomer can be used for adjusting the cohesive force of an adhesive layer when the medical adhesive of the present invention is used for a medical adhesive tape or sheet and the like, improving the compatibility with an organic liquid component, and the like. The amount thereof to be used can be freely determined by substituting a part of the content of (meth)acrylic acid alkyl ester according to the object.

Examples of the monomer copolymerizable with (meth) acrylic acid alkyl ester other than the silane monomer and the carboxyl group-containing monomer include sulfoxyl group-containing monomers such as styrene sulfonic acid, allyl sulfonic acid, sulfopropyl(meth)acrylate, (meth)acryloyloxynaphthalenesulfonic acid, acrylamidemethylpropanesulfonic acid and the like, hydroxyl group-containing monomers such as (meth)acrylic acid hydroxyethyl ester, (meth) acrylic acid hydroxypropyl ester and the like, amide group-containing monomers such as (meth)acrylamide, dimethyl (meth)acrylamide, N-butylacrylamide, N-methylol(meth) acrylamide, N-methylolpropane(meth)acrylamide and the like, (meth)acrylic acid alkylaminoalkyl esters such as (meth) acrylic acid aminoethyl ester, (meth)acrylic acid dimethylaminoethyl ester, (meth)acrylic acid tert-butylaminoethyl ester and the like, (meth)acrylic acid alkoxyalkyl esters such as (meth)acrylic acid methoxyethyl ester, (meth)acrylic acid ethoxyethyl ester and the like, alkoxy group (or ether bond on side chain)-containing (meth)acrylic acid esters such as (meth)acrylic acid methoxyethyleneglycol ester, (meth) acrylic acid tetrahydrofurfuryl ester, (meth)acrylic acid methoxyethyleneglycol ester, (meth)acrylic acid methoxydiethyleneglycol ester, (meth)acrylic acid methoxypolyethyleneglycol ester, (meth)acrylic acid methoxypolypropyleneglycol ester and the like, vinyl monomers such as (meth)acrylonitrile, vinyl acetate, vinyl propionate, N-vinyl-2-pyrrolidone, methylvinylpyrrolidone, vinylpyridine, vinylpiperidine, vinylpyrimidine, vinylpiperazine, vinylpyrazine, vinylpyrrole, vinylimidazole, vinylcaprolactam, vinyloxazole, vinylmorpholine and the like, and the like can be mentioned. They may be used alone or in combination of two or more kinds thereof. Particularly, hydroxyl group-containing monomer and (meth)acrylic acid alkoxyalkyl ester are preferable.

The water-dispersed copolymer constituting the medical adhesive of the present invention is made of a water-dispersion of a copolymer obtained by copolymerization of the aforementioned monomers and can be prepared, for example, as a water-dispersion of (meth)acrylic acid alkyl ester copolymer by subjecting a mixture of a monomer mixture containing (meth)acrylic acid alkyl ester, and a silane monomer to general emulsion polymerization.

The amount of water as a dispersion medium to be used in a water-dispersed copolymer is generally about 50-400 parts by weight per 100 parts by weight of the solid content of the water-dispersed copolymer.

As the polymerization method, general en bloc polymerization, continuous dropping polymerization, portion-wise dropping polymerization and the like can be employed, and the polymerization temperature is, for example, about 20-100° C., preferably about 20-80° C. While the polymerization time varies depending on the polymerization method, it is generally about 3-24 hr.

Examples of the polymerization initiator to be used for the polymerization include, but not limited to, azo initiators such as 2,2'-azobisisobutyronitrile, 2,2'-azobis(2-methylpropionamidine) disulfate, 2,2'-azobis(2-amidinopropane)dihydrochloride, 2,2'-azobis[2-(5-methyl-2-imidazolin-2-yl)propane]dihydrochloride, 2,2'-azobis(N,N'-dimethyleneisobutylamidine), 2,2'-azobis[N-(2-carboxyethyl)-2-methylpropionamidine]hydrate and the like; persulfate such as potassium persulfate, ammonium persulfate and the like; peroxide initiators such as benzoyl peroxide, tert-butyl hydroperoxide, hydrogen peroxide and the like; substituted ethane initiators such as phenyl-substituted ethane and the like; aromatic carbonyl compounds; redox initiators such as a combination of persulfate and sodium bisulfite, a combination of peroxide and sodium ascorbate and the like; and the like, with preference given to azo initiators. The amount of the polymerization initiator to be used is, for example, about 0.005-1 part by weight per 100 parts by weight of the above-mentioned monomer mixture containing (meth)acrylic acid alkyl ester.

For emulsion polymerization, a chain transfer agent may be used to control the degree of polymerization. Examples of the chain transfer agent include general chain transfer agents, such as mercaptans (e.g., dodecanethiol and the like), and the like. The amount of the chain transfer agent to be used is, for example, about 0.001-0.5 part by weight, per 100 parts by weight of the above-mentioned monomer mixture containing (meth)acrylic acid alkyl ester. For balancing skin fixability and low skin irritation, it is preferably 0.01-0.4 part by weight, particularly preferably 0.01-0.04 part by weight.

As the emulsifier, anionic emulsifiers such as sodium lauryl sulfate, lauryl ammonium sulfate, sodium dodecylbenzene sulfonate, sodium polyoxyethylenealkylether sulfate (e.g., sodium polyoxyethylenelaurylether sulfate), ammonium polyoxyethylenealkylether sulfate (e.g., ammonium polyoxyethylenelaurylether sulfate), ammonium polyoxyethylenealkylphenylether sulfate, ammonium polyoxyethylenealkylphenylether sulfate, sodium polyoxyethylenealkylphenylether sulfate and the like; nonionic emulsifiers such as polyoxyethylene alkyl ether, polyoxyethylene alkyl phenyl ether and the like, and the like can be used. The emulsifiers may be used alone or in combination of two or more kinds thereof. The amount of the emulsifier to be used is, for example, 0.2-10 parts by weight, preferably about 0.5-5 parts by weight, per 100 parts by weight of the above-mentioned monomer mixture containing (meth)acrylic acid alkyl ester.

The water-dispersed copolymer constituting the medical adhesive of the present invention may be prepared, in addition to the above-mentioned method, by obtaining a copolymer of a monomer mixture containing (meth)acrylic acid ester and a silane monomer by a method other than the emulsion polymerization and dispersing the copolymer in water by an emulsifier.

The medical adhesive of the present invention contains an organic liquid component compatible with the above-mentioned water-dispersed copolymer.

By adding an organic liquid component to the water-dispersed copolymer, the modulus in the low strain level of the adhesive can be decreased, good adhesiveness to the skin can be maintained, damage to the stratum corneum upon peeling can be reduced and the pain upon peeling can also be reduced.

The organic liquid component to be used for the medical adhesive of the present invention needs to be liquid at ambient temperature and shows good compatibility with water-dispersed copolymer, and preferably, is not easily transferred to medical instrument, medical device and the like when in use.

In the present invention, being "compatible" means that organic liquid component is uniformly dissolved in a water-dispersed copolymer, where a visual confirmation of separation is not possible.

In the medical adhesive of the present invention, examples of preferable organic liquid component include an ester of monobasic acid or polybasic acid having 8 to 18 carbon atoms and branched alcohol having 14 to 18 carbon atoms and an ester of straight chain or branched chain saturated or unsaturated fatty acid having 12 to 18 carbon atoms (particularly straight chain or branched chain unsaturated fatty acid having 14 to 18 carbon atoms) and alcohol of quadrivalence or below.

When monobasic acid or polybasic acid having less than 8 carbon atoms is used, transferability to medical instrument, medical device and the like may become higher, and when monobasic acid or polybasic acid having more than 18 carbon atoms is used, the compatibility with water-dispersed copolymer may be degraded and good adhesive property may not be afforded. Thus, use of monobasic acid or polybasic acid having 8 to 18 carbon atoms is preferable.

When branched alcohol having less than 14 carbon atoms, which is liquid at room temperature, is used, and the support of a medical adhesive tape or sheet is a material permitting transfer of plasticizer such as unplasticized polyvinyl chloride, the plasticizer may be transferred. When branched alcohol having more than 18 carbon atoms is used, the compatibility with water-dispersed copolymer may be degraded. Thus, use of branched alcohol having 14 to 18 carbon atoms is preferable.

Examples of the ester of monobasic acid or polybasic acid having 8 to 18 carbon atoms and branched alcohol having 14 to 18 carbon atoms include isostearyl laurate, isocetyl myristate, octyldodecyl myristate, isostearyl palmitate, isocetyl stearate, octyldodecyl oleate, diisostearyl adipate, diisocetyl sebacate, trioleyl trimellitate, triisocetyl trimellitate and the like.

Examples of straight chain or branched chain saturated or unsaturated fatty acid having 12 to 18 carbon atoms include myristoyleic acid, oleic acid, linoleic acid, linolenic acid, isopalmitic acid, isostearic acid, lauric acid and the like, and examples of alcohol of quadrivalence or below include ethyleneglycol, propyleneglycol, glycerol, trimethylolpropane, pentaerythritol, sorbitan and the like.

Examples of the ester of straight chain or branched chain saturated or unsaturated fatty acid having 12 to 18 carbon atoms and alcohol of quadrivalence or below include sorbitan trioleate, sorbitan monooleate, sorbitan monolaurate and the like.

The medical adhesive of the present invention preferably contains 10-100 parts by weight, more preferably 20-80 parts by weight, of the organic liquid component per 100 parts by weight of the above-mentioned water-dispersed copolymer.

The medical adhesive of the present invention can be obtained by applying an adhesive composition containing the above-mentioned water-dispersed copolymer and the above-mentioned organic liquid component to a support, release liner and the like, and drying the same. The drying temperature is generally about 80-140° C., preferably about 90-130° C. and drying time is generally about 1-10 min. By the above-mentioned drying by heating treatment, crosslinking by a silane monomer can be performed. The medical adhesive of the present invention has a thickness after drying of generally about 10-150 μm, preferably about 30-70 μm.

When an adhesive composition is applied to a support or release liner, a thickener may be added as necessary to facilitate the application. Examples of the thickener include Primal ASE-60 (manufactured by ROHM AND HAAS JAPAN KK.), ARON B-500 (manufactured by TOAGOSEI CO., LTD) and the like.

In the first medical adhesive of the present invention, an adhesive is preferably formed by adding an organic liquid component to a water-dispersed copolymer having an insoluble content of 30-80 wt %. In other words, in the first medical adhesive of the present invention, the gel fraction of the water-dispersed copolymer after crosslinking is preferably adjusted to 30-80 wt %.

As described, since the medical adhesive of the present invention uses a water-dispersed copolymer crosslinked by a silane monomer, the cohesive force of the adhesive can be improved and suitable adhesive force can be expressed.

In the present invention, the "gel fraction of the water-dispersed copolymer after crosslinking" means a gel fraction of the water-dispersed copolymer in the adhesive crosslinked by a silane monomer.

Here, in the present invention, the gel fraction of water-dispersed copolymer is a value measured and calculated by the following method.

(Measurement Method of Gel Fraction)

An adhesive (sample) is taken by about 0.04 g and the weight ($W_1$) is accurately measured. The sample is immersed in ethyl acetate at ambient temperature for 7 days and the solvent soluble content is extracted. The residue (insoluble content) is filtered through a polytetrafluoroethylene membrane having an average pore size of 0.2 μm (e.g., TEMISH manufactured by NITTO DENKO CORPORATION), dried at 130° C. for 1 hr, the weight ($W_2$) is measured and the insoluble content (wt %) is determined from the following formula.

$$\text{gel fraction (\%)} = (W_2 \times 100)/(W_1 \times A/B)$$

A=weight of (water-dispersed copolymer+crosslinking agent)

B=weight of (water-dispersed copolymer+organic liquid component+crosslinking agent)

In the above-mentioned formulas A and B, the "crosslinking agent" means a crosslinking agent other than a silane monomer, which is contained in the adhesive.

In the first medical adhesive of the present invention, the gel fraction of the water-dispersed copolymer after crosslinking is preferably 30-80 wt %, more preferably 40-70 wt %.

When the gel fraction is less than 30 wt % (particularly, less than 40 wt %), the cohesive force of the adhesive becomes insufficient. As a result, the adhesive may remain on the skin upon peeling and the adhesive may ooze off of the side of a medical adhesive tape or sheet. When the support is a porous support such as non-woven fabric and the like, the adhesive penetrates the support. On the other hand, when the gel fraction exceeds 80 wt %, sufficient skin adhesive strength may not be obtained.

In the second medical adhesive of the present invention, the gel fraction after crosslinking is adjusted to 40-80 wt %, preferably 40-70 wt %, by adding an organic liquid component compatible with the above-mentioned water-dispersed copolymer and performing crosslinking by a silane monomer.

As a result, the medical adhesive of the present invention becomes a low skin irritant medical adhesive wherein the organic liquid component is uniformly dissolved in the water-dispersed copolymer. Moreover, since a water-dispersed copolymer is crosslinked by a silane monomer, the medical adhesive of the present invention shows an improved cohesive force and can express a suitable adhesive force.

When the above-mentioned gel fraction of the water-dispersed copolymer after crosslinking is less than 40 wt %, the cohesive force of the adhesive becomes insufficient. As a result, the adhesive may remain on the skin upon peeling and the adhesive may ooze off of the side of a medical adhesive tape or sheet. When the support is a porous support such as non-woven fabric and the like, the adhesive penetrates the support. On the other hand, when the gel fraction of the water-dispersed copolymer after crosslinking exceeds 80 wt %, a sufficient skin adhesive strength may not be obtained.

In the first medical adhesive of the present invention, the weight average molecular weight of the above-mentioned sol component of the water-dispersed copolymer after crosslinking is preferably not less than 300000, more preferably not less than 400000.

In the second medical adhesive of the present invention, the weight average molecular weight of the above-mentioned sol component of the water-dispersed copolymer after crosslinking is not less than 300000, preferably not less than 400000. When it is less than 300000, the fixing performance may be degraded and sufficient adhesiveness may not be obtained.

In the present invention, the "sol component of the water-dispersed copolymer after crosslinking" means the sol component of the water-dispersed copolymer in the adhesive crosslinked by a silane monomer.

In the medical adhesive of the present invention, the gel fraction of water-dispersed copolymer before crosslinking is preferably adjusted to not more than 30 wt %, more preferably not more than 28 wt %. When the gel fraction before crosslinking exceeds 30 wt %, a pain upon peeling and a damage such as separation of stratum corneum to the skin tend to occur easily.

In the present invention, the "gel fraction of water-dispersed copolymer before crosslinking" means the gel fraction of the water-dispersed copolymer in the adhesive free of crosslinking. To be specific, the "gel fraction of water-dispersed copolymer before crosslinking" means the gel fraction of the water-dispersed copolymer in the adhesive produced under the same conditions as the medical adhesive of the present invention except that a silane monomer copolymerizable with (meth)acrylic acid alkyl ester is not used.

Furthermore, in the medical adhesive of the present invention, the weight average molecular weight/number average molecular weight (that is, molecular weight distribution) of a sol component of the water-dispersed copolymer after crosslinking is preferably 3-7, more preferably 3-5. When the value is less than 3, the molecular weight distribution becomes too small to exert the desired properties, and when it exceeds 7, the content ratio of the low molecular weight copolymer increases and the desired properties may not be expressed.

Here, in the present invention, the weight average molecular weight and the weight average molecular weight/number average molecular weight (rate) of a sol component of the water-dispersed copolymer are values measured and calculated by the following method.

(Measurement Method of Molecular Weight of Sol Component)

An adhesive (sample) (about 0.04 g) is taken, the sample is immersed in ethyl acetate at ambient temperature for 7 days, insoluble content is removed, and the obtained solvent soluble content is dried to give a tetrahydrofuran solution having a concentration of 1.0 g/L. The solution is filtered through a membrane filter having a pore size of 0.45 μm, the filtrate (100 μl) is applied to gel permeation chromatography (e.g., analysis apparatus: TOSOH HLC-8120GPC (manufactured by TOSOH CORPORATION), column: TSK gel GMH-H(s), two, flow rate 0.5 ml/min, column temperature 40° C., detector RI) and the retention time is measured. The molecular weight is calculated based on polystyrene, and the molecular weight and molecular weight distribution (weight average molecular weight/number average molecular weight) of a polymer having a weight average molecular weight of not less than 10000 is evaluated.

The gel fraction, the weight average molecular weight of a sol component, and the weight average molecular weight/number average molecular weight of a sol component can be controlled by appropriately selecting the ratio of the monomer mixture containing (meth)acrylic acid alkyl ester and a silane monomer, the amount of the carboxyl group-containing monomer to be added, the amount of the chain transfer agent to be used and the like from, for example, the aforementioned preferable ranges, in the production of a medical adhesive.

The medical adhesive tape and sheet of the present invention contains the medical adhesive of the present invention at least on one surface of the support. In other words, the medical adhesive tape and sheet of the present invention has an adhesive layer comprising the medical adhesive of the present invention at least on one surface of the support.

That is, the medical adhesive tape and sheet of the present invention can be produced by direct applying, to one or both surfaces of the support, the aforementioned adhesive composition containing a water-dispersed copolymer and an organic liquid component, which is mentioned as regards the medical adhesive of the present invention, and drying the same, or forming an adhesive layer made of the medical adhesive of the present invention on a support by adhering, to a support, a substance obtained by coating and drying the adhesive composition on a release liner. The drying temperature is generally about 80-140° C., preferably about 90-130° C., and the drying time is generally about 1-10 min. By the above-mentioned heating and drying treatments, crosslinking by a silane monomer can be performed. The adhesive layer has a thickness after drying of generally about 10-150 μm, preferably about 30-70 μm.

In addition, the medical adhesive tape of the present invention can also be obtained by preparing a medical adhesive sheet of the present invention and cutting same into a tape.

When an adhesive composition is to be applied to a support or release liner, a thickener may be added as necessary to facilitate the application. Examples of the thickener include Primal ASE-60 (manufactured by ROHM AND HAAS JAPAN KK.), ARON B-500 (manufactured by TOAGOSEI CO., LTD) and the like.

While the support to be used in the present invention is not particularly limited as long as it can maintain the medical adhesive layer of the present invention, for example, film, tape or sheet support used for adhesive bandage, surgical tape, first-aid adhesive tape, adhesive tape of a large size, dressing material, cataplasm and the like can be used. These supports may be porous or non-porous.

The thickness of the support is not particularly limited and is appropriately selected according to the use. It is generally about 30-300 μm.

The medical adhesive tape and sheet of the present invention may carry a drug to give a transdermal patch or transdermally absorptive preparation. The drug to be carried is not particularly limited as long as it can be carried on the adhesive of the present invention.

EXAMPLES

The present invention is explained in detail in the following by referring to Examples which are not to be construed as limitative.

Example 1

2-Ethylhexyl acrylate (86.5 parts by weight), methyl methacrylate (9.6 parts by weight), acrylic acid (3.9 parts by weight), 3-methacryloyloxypropyltrimethoxysilane (0.05 part by weight), 1-dodecanethiol (0.05 part by weight), sodium polyoxyethylenelaurylether sulfate (3 parts by weight) and water (44.2 parts by weight) were emulsified in a homo mixer to give a monomer emulsion. The above-mentioned monomer emulsion (5.2 parts by weight) and water (56.3 parts by weight) were placed in a reaction container (separable flask) equipped with a condenser, a nitrogen inlet tube, a thermometer and a stirrer and the mixture was stirred for 1 hr while introducing an inert gas. Then, 2,2'-azobis[N-(2-carboxyethyl)-2-methylpropionamidine]hydrate (0.1 part by weight) was added as a polymerization initiator and the mixture was reacted at 60° C. for 1 hr. The above-mentioned monomer emulsion (141.1 parts by weight) was added dropwise at 60° C. for 4 hr, and the mixture was aged further at the same temperature for 3 hr, and aqueous ammonia was added to adjust to pH 7 to give a water-dispersed copolymer. Sorbitan trioleate (30 parts by weight) was added as an organic liquid component to 100 parts by weight of the water-dispersed copolymer (solid content) to give an adhesive.

A thickener (Primal ASE-60 (manufactured by ROHM AND HAAS JAPAN KK., 0.5 part by weight) was added to the obtained adhesive (100 parts by weight) and the adhesive having increased viscosity was applied to a release liner to afford a thickness after drying of 40 μm and dried at 130° C. for 3 min. The obtained laminate was adhered to polyester/pulp blended non-woven fabric (23 g/m$^2$) to give an adhesive sheet.

Example 2

An adhesive sheet was obtained in the same manner as in Example 1 except that the amount of 3-methacryloyloxypropyltrimethoxysilane was changed to 0.02 part by weight and the amount of 1-dodecanethiol was changed to 0.02 part by weight.

Example 3

An adhesive sheet was obtained in the same manner as in Example 1 except that the amount of 3-methacryloyloxypropyltrimethoxysilane was changed to 0.08 part by weight and the amount of acrylic acid was changed to 5 parts by weight.

Example 4

An adhesive sheet was obtained in the same manner as in Example 1 except that 3-methacryloyloxypropyltrimethoxysilane was changed to 3-acryloyloxypropyltrimethoxysilane.

Example 5

An adhesive sheet was obtained in the same manner as in Example 1 except that 3-methacryloyloxypropyltrimethoxysilane was changed to 3-methacryloyloxypropyltriethoxysilane.

Example 6

An adhesive sheet was obtained in the same manner as in Example 2 except that the amount of acrylic acid was changed to 2 parts by weight.

Example 7

An adhesive sheet was obtained in the same manner as in Example 1 except that 2-ethylhexyl acrylate was changed to isononyl acrylate and methyl methacrylate was changed to ethyl methacrylate.

Comparative Example 1

An adhesive sheet was obtained in the same manner as in Example 1 except that the amount of sorbitan trioleate was changed to 40 parts by weight and an epoxy crosslinking agent, TEPIC-S (manufactured by NISSAN CHEMICAL INDUSTRIES, LTD) (0.2 part by weight), was added as a crosslinking agent, without adding 3-methacryloyloxypropyltrimethoxysilane.

Comparative Example 2

An adhesive sheet was obtained in the same manner as in Example 1 except that the crosslinking agent of Comparative Example 1 was changed to an epoxy crosslinking agent, DENACOL EX-321 (manufactured by Nagase ChemteX Corporation, 0.2 part by weight).

Comparative Example 3

An adhesive sheet was obtained in the same manner as in Example 1 except that the crosslinking agent of Comparative Example 1 was changed to oxazoline crosslinking agent, EPOCROS WS-700 (manufactured by NIPPON SHOKUBAI CO., LTD.) in a solid content of 0.2 part by weight.

Comparative Example 4

Under an inert gas atmosphere, a monomer mixture comprising 2-ethylhexyl acrylate (95 parts by weight) and acrylic acid (5 parts by weight) was polymerized in ethyl acetate to give an acrylic polymer. The solid content (100 parts by weight) of the acrylic polymer was mixed with sorbitan trioleate (40 parts by weight) and trifunctional isocyanate (CORONATE L (trade name), manufactured by NIPPON POLYURETHANE INDUSTRY CO., LTD., 0.33 part by weight) as a crosslinking agent in ethyl acetate to give an adhesive solution. An adhesive sheet was obtained in the same manner as in Example 1 using this adhesive solution.

Comparative Example 5

An adhesive sheet was obtained in the same manner as in Example 1 except that 3-methacryloyloxypropyltrimethoxysilane was not added.

Comparative Example 6

An adhesive sheet was obtained in the same manner as in Example 1 except that the amount of 3-methacryloyloxypropyltrimethoxysilane was changed to 3 parts by weight and the amount of 1-dodecanethiol was changed to 0.08 part by weight.

Comparative Example 7

An adhesive sheet was obtained in the same manner as in Example 1 except that acrylic acid was not added.

Example 8

2-Ethylhexyl acrylate (86.5 parts by weight), methyl methacrylate (9.6 parts by weight), acrylic acid (3.9 parts by weight), 3-methacryloyloxypropyltrimethoxysilane (0.05 part by weight), 1-dodecanethiol (0.035 part by weight), sodium polyoxyethylenelaurylether sulfate (3 parts by weight), and water (44.2 parts by weight) were emulsified in a homo mixer to give a monomer emulsion. The above-mentioned monomer emulsion (5.2 parts by weight) and water (56.3 parts by weight) were placed in a reaction container (separable flask) equipped with a condenser, a nitrogen inlet tube, a thermometer and a stirrer and the mixture was stirred for 1 hr while introducing an inert gas. Then, 2,2'-azobis[N-(2-carboxyethyl)-2-methylpropionamidine]hydrate (0.1 part by weight) was added as a polymerization initiator and the mixture was reacted at 60° C. for 1 hr. The above-mentioned monomer emulsion (141.1 parts by weight) was added dropwise at 60° C. for 4 hr, and the mixture was aged further at the same temperature for 3 hr, and aqueous ammonia was added to adjust to pH 7 to give a water-dispersed copolymer. Sorbitan trioleate (30 parts by weight) was added as an organic liquid component to 100 parts by weight of the water-dispersed copolymer (solid content) to give an adhesive.

A thickener (Primal ASE-60 (manufactured by ROHM AND HAAS JAPAN KK., 0.5 part by weight) was added to the obtained adhesive (100 parts by weight) and the adhesive having increased viscosity was applied to a release liner to afford a thickness after drying of 40 μm and dried at 130° C. for 3 min. The obtained laminate was adhered to polyester/pulp blended non-woven fabric (23 g/m$^2$) to give an adhesive sheet.

Example 9

An adhesive sheet was obtained in the same manner as in Example 8 except that 3-methacryloyloxypropyltrimethoxysilane was changed to 3-acryloyloxypropyltrimethoxysilane.

Example 10

An adhesive sheet was obtained in the same manner as in Example 8 except that 3-methacryloyloxypropyltrimethoxysilane was changed to 3-methacryloyloxypropyltriethoxysilane.

Example 11

An adhesive sheet was obtained in the same manner as in Example 8 except that sorbitan trioleate was changed to sorbitan monolaurate.

Example 12

An adhesive sheet was obtained in the same manner as in Example 8 except that sorbitan trioleate was changed to sorbitan monooleate.

Comparative Example 8

An adhesive sheet was obtained in the same manner as in Example 8 except that a polymerization initiator, 2,2'-azobis[N-(2-carboxyethyl)-2-methylpropionamidine]hydrate of Example 8 was changed to ammonium persulfate (0.1 part by weight) and TEPIC-S (NISSAN CHEMICAL INDUSTRIES, LTD) (0.2 part by weight) was added as a crosslinking agent, without using 3-methacryloyloxypropyltrimethoxysilane.

Experimental Example 1

The adhesive sheets obtained in Examples 1-7 and Comparative Examples 1-7 were examined for the following properties (in each test, n=3).

Insoluble Content (Gel Fraction) in an Adhesive

An adhesive in each sample was taken (about 0.04 g) and the weight ($W_1$) was accurately measured. The sample was immersed in ethyl acetate at 23° C. for 7 days, and a solvent soluble content was extracted. The insoluble content was taken, the weight ($W_2$) after drying at 130° C. for 1 hr was measured, and the insoluble content (wt %) was determined from the following formula.

$$(W_2 \times 100)/(W_1 \times A/B)$$

A=weight of (water-dispersed copolymer+crosslinking agent)

B=weight of (water-dispersed copolymer+organic liquid component+crosslinking agent)

Adhesive Strength Test

A sample cut into width 12 mm, length 50 mm was press-adhered to a bakelite board by one reciprocation of a 2 kg roller and, after 30 min, the sample was peeled off at a peel angle 180°, rate 300 mm/min and the release force at that time was measured.

Fixing Performance Test (Normal State)

A vinyl chloride tube (inner diameter 3 mm, outer diameter 5 mm, length 70 mm) bent to form a circular arc of diameter 20 mm was fixed with a sample cut into width (12 mm), length (55 mm) on the arm of a test subject. The adhesion state after the lapse of 6 hr was visually evaluated. For evaluation, a sample completely free of peeling off and a sample released in the part covering the center of the circular arc but fixing the tube to stay thereon without extruding from the both ends of the sample were marked with ○, and the rest was marked with x.

Fixing Performance Test (Perspiration Resistance)

Each sample was fixed on the arm of a test subject under the same conditions as in the fixing performance test (normal state). The adhesion state after the test subject was left under 45° C./95% R.H. for 1 hr was visually evaluated. For evaluation, a sample completely free of peeling off and a sample released in the part covering the center of the circular arc but fixing the tube to stay thereon without extruding from the both ends of the sample were marked with ○, and the rest was marked with x.

Skin Irritation

Evaluation was made based on the pain when a sample was peeled off from the back of the test subject after 6 hr of adhesion. When the pain was absent or slightly felt but not painful upon peeling off, ○ was given, and when the pain was painful, x was given.

TABLE 1

|  | gel fraction (%) | adhesive strength (N/12 mm) | fixing performance (normal state) | fixing performance (perspiration resistance) | skin irritation |
|---|---|---|---|---|---|
| Ex. 1 | 51 | 1.6 | ○ | ○ | ○ |
| Ex. 2 | 52 | 1.9 | ○ | ○ | ○ |
| Ex. 3 | 48 | 1.6 | ○ | ○ | ○ |
| Ex. 4 | 41 | 2.2 | ○ | ○ | ○ |
| Ex. 5 | 55 | 1.9 | ○ | ○ | ○ |
| Ex. 6 | 50 | 1.1 | ○ | ○ | ○ |
| Ex. 7 | 53 | 1.5 | ○ | ○ | ○ |
| Comp. Ex. 1 | 48 | 1.7 | x | x | ○ |
| Comp. Ex. 2 | 43 | 2.6 | x | x | ○ |
| Comp. Ex. 3 | 43 | 2.3 | x | x | ○ |
| Comp. Ex. 4 | 64 | 1.1 | ○ | x | ○ |
| Comp. Ex. 5 | 28 | 4.0 | x | x | x |
| Comp. Ex. 6 | 77 | 0.6 | x | x | ○ |
| Comp. Ex. 7 | 32 | 3.2 | x | x | x |

From the results of Table 1 above, it is clear that the medical adhesive and medical adhesive sheet of the present invention is superior in the fixing performance (normal state and perspiration resistance), causes low skin irritation, and has adequate adhesive strength.

Experimental Example 2

The adhesive sheets obtained in Examples 8-12 and Comparative Example 8 were examined for the following properties (in each test, n=3).

Insoluble Content (Gel Fraction) of Adhesive after Crosslinking

An adhesive in each sample of Examples and Comparative Example was taken (about 0.04 g) and the weight ($W_1$) was accurately measured. The sample was immersed in ethyl acetate at ambient temperature for 7 days, and a solvent soluble content was extracted. The residue (insoluble content) was filtered through a polytetrafluoroethylene membrane (average pore size 0.2 μm, manufactured by NITTO DENKO CORPORATION, TEMISH), the weight ($W_2$) after drying at 130° C. for 1 hr was measured, and the insoluble content (wt %) was determined from the following formula.

$$(W_2 \times 100)/(W_1 \times A/B)$$

A=weight of (water-dispersed copolymer+crosslinking agent)

B=weight of (water-dispersed copolymer+organic liquid component+crosslinking agent)

Insoluble Content (Gel Fraction) of Adhesives Before Crosslinking of Examples 8-12

An adhesive sheet was obtained in the same manner as in Examples 8-12 except that 3-methacryloyloxypropyltrimethoxysilane, 3-acryloyloxypropyltrimethoxysilane or 3-methacryloyloxypropyltriethoxysilane were not used. The gel fraction of the adhesive in the obtained adhesive sheet was evaluated according to the measurement of insoluble content of adhesive after crosslinking. As a result, the gel fraction was 26%. The gel fraction was taken as the gel fraction before crosslinking of Examples 8-12.

Insoluble Content (Gel Fraction) of Adhesive Before Crosslinking of Example 8

An adhesive sheet was obtained in the same manner as in Comparative Example 8 except that TEPIC-S was not used. The gel fraction of the adhesive in the obtained adhesive sheet was evaluated according to the measurement of insoluble content of adhesive after crosslinking. As a result, the gel fraction was 50%. The gel fraction was taken as the gel fraction of Comparative Example.

Measurement of Sol Component Molecular Weight

The extract (soluble content) obtained in the gel fraction measurement was dried to give a tetrahydrofuran solution having a concentration of 1.0 g/L. The solution was filtered through a membrane filter having a pore size of 0.45 μm, the filtrate (100 μl) is applied to gel permeation chromatography (analysis apparatus: TOSOH HLC-8120GPC (manufactured by TOSOH CORPORATION), column: TSK gel GMH-H(s), two, flow rate 0.5 ml/min, column temperature 40° C., detector RI) and the retention time is measured. The molecular weight was calculated based on polystyrene, and the molecular weight and molecular weight distribution (weight average molecular weight/number average molecular weight) of a polymer having a weight average molecular weight of not less than 10000 was evaluated.

Adhesive Strength Test

Measured in the same manner as in Experimental Example 1.

Fixing Performance Test (Normal State)

The test and evaluation were performed in the same manner as in Experimental Example 1.

Fixing Performance Test (Perspiration Resistance)

The test and evaluation were performed in the same manner as in Experimental Example 1.

Skin Irritation

The test and evaluation were performed in the same manner as in Experimental Example 1.

TABLE 2

|  | gel fraction (%) before crosslinking | gel fraction (%) after crosslinking | sol component molecular weight | weight average molecular weight/number average molecular weight | adhesive strength (N/12 mm) | fixing performance (normal state) | fixing performance (perspiration resistance) | skin irritation |
| --- | --- | --- | --- | --- | --- | --- | --- | --- |
| Example 8 | 26 | 51 | 499000 | 4.0 | 1.6 | ○ | ○ | ○ |
| Example 9 | 26 | 41 | 550000 | 4.3 | 1.6 | ○ | ○ | ○ |
| Example 10 | 26 | 55 | 460000 | 4.0 | 1.7 | ○ | ○ | ○ |
| Example 11 | 26 | 54 | 499000 | 4.0 | 1.4 | ○ | ○ | ○ |
| Example 12 | 26 | 50 | 499000 | 4.0 | 1.4 | ○ | ○ | ○ |
| Comparative Example 8 | 50 | 61 | 286000 | 3.8 | 1.3 | x | x | ○ |

From the results of Table 2 above, it is clear that the medical adhesive and medical adhesive sheet of the present invention are superior in the fixing performance (normal state and perspiration resistance), causes low skin irritation, and has adequate adhesive strength.

This application is based on patent application Nos. 2006-144, 2006-276941 and 2006-298209 filed in Japan, the contents of which are incorporated in full herein by this reference.

The invention claimed is:

1. A medical adhesive comprising a water-dispersed copolymer obtained by copolymerizing 100 parts by weight of a monomer mixture containing (meth)acrylic acid alkyl ester and 0.005-2 parts by weight of a silane monomer copolymerizable with the (meth)acrylic acid alkyl ester in 100 parts by weight of the monomer mixture containing (meth) acrylic acid alkyl ester, and
an organic liquid component compatible with the water-dispersed copolymer.

2. The medical adhesive of claim 1, wherein the monomer mixture containing the (meth)acrylic acid alkyl ester comprises 0.1-10 parts by weight of a carboxyl group-containing monomer copolymerizable with the (meth)acrylic acid alkyl ester in 100 parts by weight of the monomer mixture containing the (meth)acrylic acid alkyl ester.

3. The medical adhesive of claim 1, wherein the water-dispersed copolymer after crosslinking has a gel fraction of 30-80 wt %.

4. A medical adhesive tape or sheet, comprising the medical adhesive of claim 1 on at least one surface of a support.

5. A medical adhesive comprising a water-dispersed copolymer obtained by copolymerizing a monomer mixture containing (meth)acrylic acid alkyl ester and a silane monomer copolymerizable with the (meth)acrylic acid alkyl ester, and
an organic liquid component compatible with the water-dispersed copolymer,
wherein the gel fraction of the water-dispersed copolymer after crosslinking is 40-80 wt %, and the weight average molecular weight of a sol component of the water-dispersed copolymer after crosslinking is not less than 300000.

6. The medical adhesive of claim 5, wherein the gel fraction of the water-dispersed copolymer before crosslinking is not more than 30 wt %.

7. The medical adhesive of claim 5, wherein weight average molecular weight/number average molecular weight of the sol component of the water-dispersed copolymer after crosslinking is 3-7.

8. The medical adhesive of claim 5, wherein the monomer mixture containing the (meth)acrylic acid alkyl ester comprises 0.1-10 parts by weight of a carboxyl group-containing monomer copolymerizable with the (meth)acrylic acid alkyl ester in 100 parts by weight of the monomer mixture containing the (meth)acrylic acid alkyl ester, and the water-dispersed copolymer is obtained by copolymerizing 0.005-2 parts by weight of the silane monomer copolymerizable with the (meth)acrylic acid alkyl ester, and 100 parts by weight of the monomer mixture containing the (meth)acrylic acid alkyl ester.

9. A medical adhesive tape or sheet, comprising the medical adhesive of claim 5 on at least one surface of a support.

10. The medical adhesive of claim 2, wherein the water-dispersed copolymer after crosslinking has a gel fraction of 30-80 wt %.

* * * * *